United States Patent
Antol et al.

Patent Number: 6,146,909
Date of Patent: Nov. 14, 2000

[54] DETECTING TRACE LEVELS OF COPPER

[75] Inventors: Joze E. Antol, Hamburg; David Gerald Coult, Bechtelsville, both of Pa.; Gustav Edward Derkits, New Providence, N.J.; Franklin Roy Dietz, Mohnton; Nur Selamoglu, Philadelphia, both of Pa.

[73] Assignee: Lucent Technologies Inc., Murray Hill, N.J.

[21] Appl. No.: 09/197,412

[22] Filed: Nov. 21, 1998

[51] Int. Cl.⁷ ....................................................... G01N 1/28
[52] U.S. Cl. .............................. 438/14; 75/726; 73/61.42
[58] Field of Search ............................ 438/14; 73/61.42, 73/61.71; 75/726; 423/326

[56] References Cited

FOREIGN PATENT DOCUMENTS

| 409145569 | 6/1997 | Japan | G01N 1/28 |
| 410307087 | 11/1998 | Japan | G01N 1/28 |

*Primary Examiner*—John F. Niebling
*Assistant Examiner*—John Murphy
*Attorney, Agent, or Firm*—Thomas, Kayden, Horstemeyer & Risley LLP

[57] ABSTRACT

The specification describes an analytical technique for determining trace levels of copper in a background matrix of titanium by dissolving the titanium and the copper impurity in HF, then selectively depositing the copper on a clean silicon surface. The silicon surface is then analyzed for the trace level of copper.

12 Claims, 1 Drawing Sheet

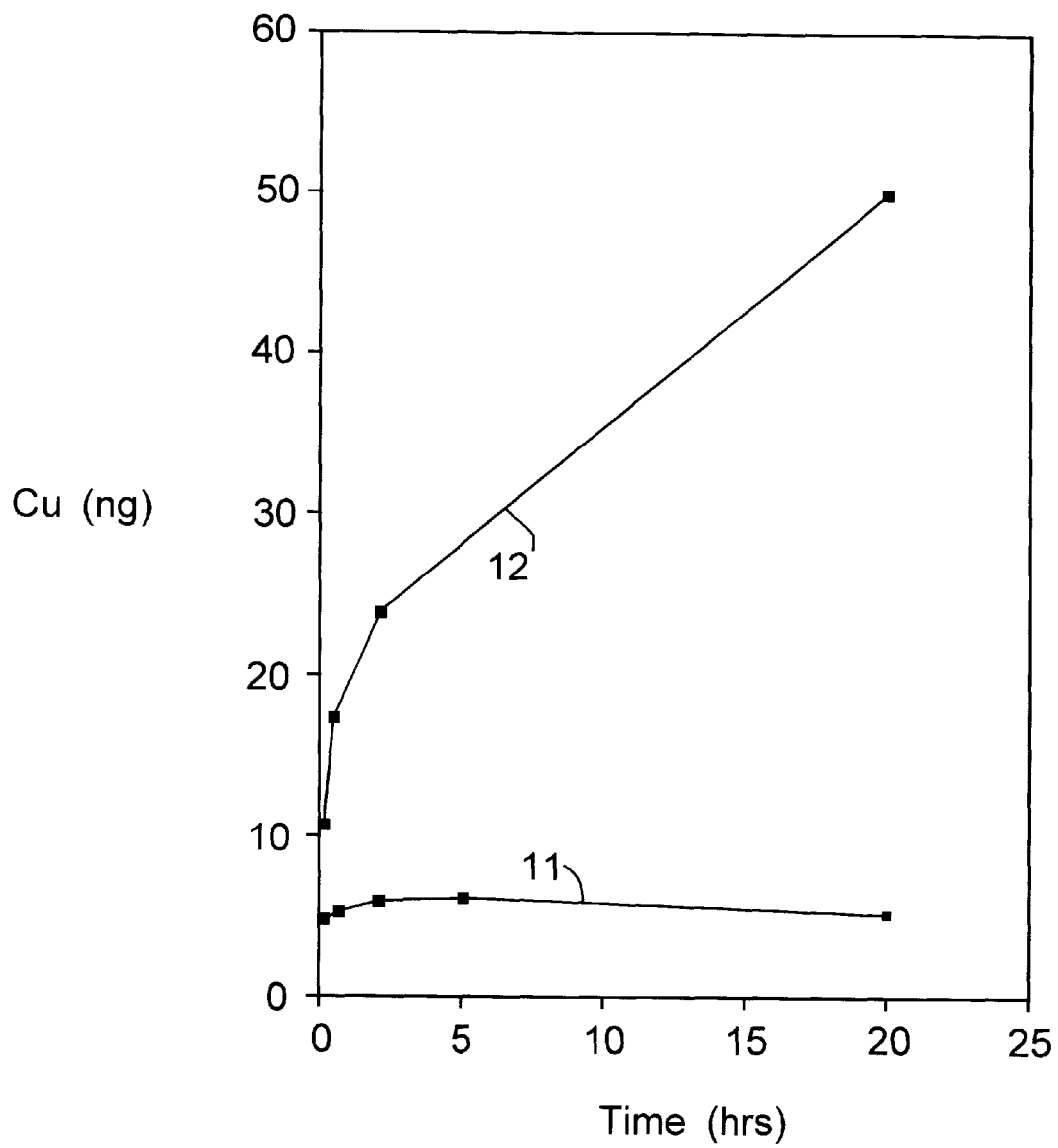

DETECTING TRACE LEVELS OF COPPER

FIELD OF THE INVENTION

This invention relates to methods for detecting trace levels of copper and is particularly applicable to the manufacture of integrated circuits.

BACKGROUND OF THE INVENTION

Trace levels of copper, as well as other metals, are known to cause failures in integrated circuits (ICs) and optoelectronic devices such as optoelectronic integrated circuits (OICs). These so-called heavy metals act as effective recombination centers and increase leakage when present in the vicinity of p-n junctions.

During the manufacture of ICs and OICs, copper and other trace metal contaminants may originate from raw materials and gases, sputtering targets, and cleaning solutions, as well as from the processing equipment used in device manufacture. These trace metals may contaminate wafer surfaces, dielectric films, or metallization layers. Often, the detection and quantification of such trace impurities by conventional analytical techniques are complicated or defeated by the presence of very high levels of metals that are intended to be incorporated in the device structure. These intended metals are referred to here as matrix elements, and the unwanted impurity metals as trace contaminants.

In conventional IC manufacture, low levels of contaminants are detected or measured using a variety of well established techniques. A typical method is to dissolve the material being investigated, or in the case of device structures partially fabricated, treat the surface of the structure with a solvent, then analyze the solution by spectrometry. An effective, and widely used, spectrometric technique is Inductively Coupled Plasma Mass Spectroscopy (ICP-MS). This is a quantitative elemental mass spectrometric technique that offers the requisite sensitivity for detecting very low levels of impurities. In some cases matrix effects arise using this technique but in general meaningful data on the trace metallic content of the materials analyzed can still be extracted.

However, when analyzing titanium metal films (after dissolution) by ICP-MS, there is major matrix interference from the titanium ions that precludes effective detection of low levels of copper. This is due to the spontaneous oxidation of titanium and the formation of oxides of isotopes of titanium, i.e. $Ti^{47}O^{16}$ and $Ti^{49}O^{16}$. The masses of these oxides are essentially equivalent to those of the isotopes of copper, i.e. $Cu^{63}$ and $Cu^{65}$, and cannot be differentiated by quadrupole mass spectrometry (they are spaced by only 0.017 amu and 0.015 amu, respectively). High resolution mass spectrometry using more expensive tools, e.g. ICP-MS instruments, may be able to discriminate the small differential, but very high resolution settings would be required, resulting in a concomitant loss of sensitivity. This mass spectral interference problem is general, affecting not only ICP-MS, but also SIMS (Secondary Ion Mass Spectrometry) and GDMS (Glow Discharge Spectrometry) techniques.

SUMMARY OF THE INVENTION

We have developed an analytical technique which relies on the separation of the interference matrix (titanium) from the analyte (copper). This is achieved by selective metal ion reduction of the analyte onto a known pure silicon surface, then analyzing the silicon surface for the analyte. The technique involves a two step solvent extraction process. The first extraction is made on the sample being analyzed to produce a solution with both the analyte and the background matrix. The separation occurs by exposing a known pure silicon surface to the solution. The analyte selectively deposits on the silicon surface leaving the bulk of the background matrix in the original solution. The silicon surface is then subjected to a second extraction process with a second solvent to dissolve the analyte. The second solvent is then analyzed for the impurity being detected. The level of the masking substance, or background matrix, on the silicon surface is sufficiently low to allow reliable data on the analyte to be obtained. Alternatively, the second solvent treatment step can be skipped and the silicon surface analyzed directly by an appropriate method such as SIMS or TXRF. The method is applicable to any combination of metals where the spectrographic signatures of the metals are not easily discriminated, and where the impurity ions and the matrix ions have sufficiently different electrochemical reduction potentials to allow separation by selective metal ion reduction.

BRIEF DESCRIPTION OF DRAWING

The FIGURE is a plot of time in hours vs. weight of copper in nanograms showing the rate of deposition for a low concentration solution and a relatively high concentration solution.

DETAILED DESCRIPTION

To demonstrate the invention, a series of silicon wafers were prepared with 1000 Angstrom titanium films on bare silicon wafers. The films were deposited by e-beam evaporation and were known to include trace levels of copper. The separation was performed as follows:

Sample wafers were placed in a high purity dilute HF solution for the first solvent extraction step. Dissolution was allowed to proceed for 2 minutes to dissolve the titanium film, and for an additional twenty minutes to ensure that metal ion impurities were allowed to reach electrochemical equilibrium with the bare silicon surface. The HF solution was analyzed and it was verified that the majority of titanium ions were in this solution.

According to the principle used in this technique, the surface of the bare silicon wafers at this point has a selective deposit of trace levels of copper. The tendency of copper to deposit from an HF solution onto a bare silicon surface is a phenomenon that has been recognized since the early days of silicon processing and in general has been regarded as an unwanted complication. Accordingly, any silicon IC processing steps that involve HF are incorporated carefully so as to minimize the possibility of copper contamination (i.e., ultra-high purity grade HF is used, and sometimes HCl is added to the HF solution to prevent copper plating). For more details on this phenomenon see e.g., "Copper Deposition on HF Etched Silicon Surfaces: Morphological and Kinetic Studies," Chyan et al., J. Electrochem. Soc. 143, 92 (1996); "A Comparative Electrochemical Study of Copper Deposition onto Silicon from Dilute and Buffered HF Acids", Li et al., J. Electrochem. Soc. 145, 241 (1998); "Mechanism of Copper Deposition on Silicon from Dilute HF Acid Solutions", Norga et al., J. Electrochem. Soc. 144, 2801 (1997); "New Method of Purification of HF Chemicals for Very Large Scale Integration Manufacturing", Yamamoto et al., J. Electrochem. Soc. 143, 4119 (1996); Selamoglu et al., J. Appl. Phys. 64, 1494 (1998). For a description of separation techniques using collectors and co-precipitants see "Separation and Preconcentration Methods in Inorganic Trace Analysis", by J. Minczewski et al.: Wiley, Chapter 3.

Referring again to the process of this invention, after the selective metal ion reduction step the surface of the silicon wafers was rinsed with deionized water, and then treated with a second solvent for the second extraction step. The solvent in this case was chosen for copper detection and was a $HNO_3/HCl$ acid mixture. This extract solution was analyzed by ICP-MS. The results on four test wafers ranged from 2 to 5 ng of copper (per wafer), while titanium levels were less than 0.01% of the original titanium quantity.

To verify that the impurities being analyzed in the procedures just outlined originated from the titanium layer, a series of bare silicon control wafers were subjected to the process just described. These showed very low or non-detectable levels of copper.

A separate experiment was performed to determine whether the copper was being collected quantitatively on the silicon wafer surface during the HF separation treatment. Titanium coated wafer pieces were treated with 10 ml of high purity dilute HF solution for various exposure times ranging from 2 minutes to 20 hours to determine whether the amount of copper collected changes with time. Another set of similar titanium coated wafer samples was also treated for the same exposure times but using copper-contaminated HF to determine whether the additional copper would also be collected on the silicon. Following HF exposure, all wafers were rinsed with DI water and treated with $HNO_3/HCl$ to extract the surface copper for measurements. The results of those measurements are shown in the FIGURE. Curve 11 represents the data for a relatively high purity solution, while curve 12 gives data for a solution deliberately contaminated with relatively high levels of copper.

The data are interpreted as follows: First, when using clean HF, the amount of copper collected on the silicon does not change with exposure time. Even at 2 minutes, which was the time required just to dissolve the titanium film, most of the copper appears to be already deposited on the silicon surface. To establish that the silicon surface has not experienced saturation with copper reference is made to the results obtained in the second part of the demonstration. These data show that in the copper-contaminated HF solution, additional copper is deposited on the silicon surface even at 2 minutes. By 20 hours, 50 ng of copper, which was 80% of the total available copper in the 10 ml solvent solution, was deposited. It will be evident to those skilled in the art that while an exposure time of 20 hours recovered large amounts of copper, the trace amounts originating from the titanium film appear to essentially completely deposit during a brief exposure, e.g. 2 minutes.

As established in the foregoing demonstration, trace levels of copper can be effectively separated from a background matrix of titanium so as to allow reliable and relatively precise detection of very low levels of these impurities. The preferred application for this technique is in testing for impurities during the manufacture of semiconductor devices. Those semiconductor devices may be semiconductor integrated circuits, or photonic devices such as lasers, optical integrated circuits, fiber amplifiers, etc. The semiconductor will be typically silicon or a III-V compound. The analytical procedure is conducted on sample wafers or control wafers that are processed through one or more stages in the wafer fabrication manufacturing line. The analysis of these test wafers may reveal a variety of conditions of interest to the process engineer. Typically the test will be run after a metal deposition step to determine if the deposition apparatus is contaminated. The deposition apparatus may be a vacuum chamber used for evaporation or sputtering. If the contamination exceeds a desired level, the apparatus may be shut down and the source of the contamination removed.

It should be evident from the foregoing that the silicon surface used to selectively deposit the copper trace impurities in the procedure described is the same surface as the semiconductor substrate on which the titanium layer is deposited. In some cases the semiconductor substrate being tested may be covered with other materials, e.g. field oxide, or interlevel dielectric, so the silicon surface used to adsorb the copper will be another silicon body, typically a bare silicon wafer. This is also the case where the semiconductor substrate on which the analysis is being conducted is another semiconductor, e.g. a III-V compound. However, it is most convenient to use a silicon wafer on which the metal layer is directly deposited as the test vehicle even if the wafer fabrication process is for III-V devices. In this way both the first solvent extraction step and the selective deposition of the target impurity occur in a single operation.

Although the silicon surfaces used in the work described here were conventional single crystal silicon wafers used in IC wafer fabrication, the technique of the invention can also be implemented using polysilicon or amorphous silicon surfaces. However, deposition occurs most efficiently on single crystal material and that is the preferred choice for the invention. It is also preferred that the material be doped to a level in the range 1–50 ohm cm. Deposition appears to occur most rapidly on p-type silicon. The use of light, for example a halogen lamp, appears to accelerate the process.

Various additional modifications of this invention will occur to those skilled in the art. All deviations from the specific teachings of this specification that basically rely on the principles and their equivalents through which the art has been advanced are properly considered within the scope of the invention as described and claimed.

We claim:

1. A method for analyzing a metal layer for one or more target impurities said method comprising the steps of:
   a. treating the metal layer with a first solvent to dissolve at least a portion of said metal layer, and to dissolve said target impurities,
   b. immersing a silicon surface in said first solvent,
   c. treating said silicon surface with a second solvent, and
   d. analyzing said second solvent for said target impurities.

2. A method for analyzing a titanium layer for copper impurities said method comprising the steps of:
   a. treating the titanium layer with an HF solution to dissolve at least a portion of said titanium layer, and to dissolve said copper impurities,
   b. immersing a silicon surface in said HF solution to selectively deposit said copper impurities on said silicon surface, leaving the predominant portion of the dissolved titanium in said HF solution,
   c. treating said silicon surface with a solvent for copper, and
   d. analyzing said solvent for copper to determine the copper content.

3. The method of claim 2 wherein said solvent for copper comprises nitric acid.

4. The method of claim 2 wherein the material of said silicon surface is selected from the group consisting of single crystal silicon, polycrystalline silicon and amorphous silicon.

5. The method of claim 4 wherein the material of said silicon surface is doped single crystal silicon.

6. A method for the manufacture of semiconductor devices comprising the steps of:
   a. placing a semiconductor substrate in a vacuum chamber,
   b. depositing a metal layer on the semiconductor substrate, said metal layer containing one or more target impurities,
   c. removing the substrate from the vacuum chamber,
   d. analyzing the substrate for one or more target impurities by the steps of:
      i. treating the surface of the substrate with a first solvent to dissolve at least a portion of said metal layer, and to dissolve said target impurities,
      ii. immersing a silicon surface in said first solvent,
      iii. analyzing said silicon surface for said target impurities,
   if the level of target impurities revealed by step d. exceeds a desired value,
   e. treating the vacuum chamber to remove a source of said target impurities.

7. The method of claim 1 wherein said semiconductor substrate is silicon and the said silicon surface is the surface of said semiconductor substrate.

8. A method for the manufacture of semiconductor devices comprising the steps of:
   a. placing a semiconductor substrate in a vacuum chamber,
   b. depositing a metal layer on the semiconductor substrate, said metal layer containing one or more target impurities,
   c. removing the substrate from the vacuum chamber,
   d. analyzing the substrate for one or more target impurities by the steps of:
      i. treating the surface of the substrate with a first solvent to dissolve at least a portion of said metal layer, and to dissolve said target impurities,
      ii. immersing a silicon surface in said first solvent,
      iii. treating said silicon surface with a second solvent,
      iv. analyzing said second solvent for said target impurities,
   if the level of target impurities revealed by step d. exceeds a desired value,
   e. treating the vacuum chamber to remove a source of said target impurities.

9. The method of claim 8 wherein said semiconductor substrate is silicon and the said silicon surface is the surface of said semiconductor substrate.

10. The method of claim 8 wherein the metal layer is titanium.

11. The method of claim 10 wherein the first solvent solution is an HF solution.

12. The method of claim 11 wherein the second solvent solution is a solvent for copper.

* * * * *